(12) United States Patent
Wang et al.

(10) Patent No.: US 7,683,147 B2
(45) Date of Patent: Mar. 23, 2010

(54) POLYMERIZATION OF OLEFINS

(75) Inventors: Lin Wang, Hockessin, DE (US); Lynda K. Johnson, Wilmington, DE (US); Alex S. Ionkin, Kennett Square, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1747 days.

(21) Appl. No.: 10/272,765

(22) Filed: Oct. 17, 2002

(65) Prior Publication Data

US 2003/0130449 A1    Jul. 10, 2003

Related U.S. Application Data

(62) Division of application No. 09/871,100, filed on May 31, 2001, now Pat. No. 6,506,861.

(60) Provisional application No. 60/214,036, filed on Jun. 23, 2000, provisional application No. 60/211,601, filed on Jun. 15, 2000, provisional application No. 60/208,087, filed on May 31, 2000.

(51) Int. Cl.
C08F 4/80    (2006.01)
C08F 4/52    (2006.01)

(52) U.S. Cl. .............. 526/161; 526/172; 526/169.1; 526/134; 526/131; 526/135; 526/348; 526/328; 526/328.5

(58) Field of Classification Search .......... 526/272, 526/134, 318, 318.3, 318.5, 172, 169, 170, 526/169.1, 262, 161
See application file for complete search history.

(56) References Cited

U.S. PATENT DOCUMENTS

| | | | |
|---|---|---|---|
| 5,527,929 A * | 6/1996 | Timmers et al. ............... 556/7 |
| 5,770,538 A * | 6/1998 | Devore et al. ............... 502/117 |
| 5,939,503 A * | 8/1999 | Goddard et al. ............ 526/134 |
| 5,942,461 A * | 8/1999 | Brown et al. ................ 502/154 |
| 6,002,032 A * | 12/1999 | Erker et al. ................... 556/11 |
| 6,060,569 A | 5/2000 | Bennett et al. |
| 6,103,658 A | 8/2000 | Mackenzie et al. |
| 6,156,857 A * | 12/2000 | Starzewski et al. ......... 526/161 |
| 6,174,975 B1 * | 1/2001 | Johnson et al. ............. 526/172 |
| 6,174,976 B1 | 1/2001 | Killian et al. |
| 6,200,925 B1 | 3/2001 | Ponasik, Jr. et al. |
| 6,303,720 B1 * | 10/2001 | Mackenzie et al. ......... 526/172 |
| 6,465,385 B1 * | 10/2002 | Sivak et al. ................. 502/152 |
| 6,541,585 B2 * | 4/2003 | Johnson et al. ............. 526/161 |

OTHER PUBLICATIONS

Desjardins, Sylvie Y. et al., Single component N-O chelated arylnickel(II) complexes as ethene Polymerisation and CO/ethene copolymerisation catalysts. Examples of ligand induced changes to the reaction pathway, Journal of Organometallic Chemistry, 1997, pp. 163-174, vol. 544.

Ittel, Steven D. et al., Late-metal catalyts for ethylene homo- and copolymerization. Chem. Rev., 2000, pp. 1169-1203, vol. 100, Published on Web Mar. 25, 2000.

Komon, Zachary J. A., et al., Synthesis of butene-ethylene and hexene-butene-ethylene copolymers from ethylene via tandem action of well-defined homogeneous catalysts, J. Am. Chem. Soc., pp. 1830-1831, vol. 122, Published on Web Feb. 10, 2000.

Komon, Zachary J. A.. et al., Synthesis, characterization, and ethylene oligomerization action of [(C6H5)2PC6H4C(O-B(C6F5)3)O-k2P,O]Ni(n3-CH2C6H5). J. Am. Soc., 2000, pp. 12379-12380, vol. 122, Published on Web Nov. 23.2000.

Kay Severine, Ralph Bergs, Michael Maurus. Sharam Miham, Wolfgang Beck; Metallkomplexe nit biologisch wichtugen Liganden, LXXV Synthese metallorganischer Cobalt (III), Iridium (III)—und Ruthenuim (II)—Komplexe mit α-Iminocarboxylat—Liganden; Aug. 26, 1004: 1995 Verlag der Zeitschrift fur Naturfirschung.

Bunyeoul Lee, Guillermo C. Mazan, Javier Vela, Zachary J. A. Komon, and Xianhui BU: α-Iminocarboxamidato—Nickel (II) Ethylene Polymerization Catalysts; Dec. 7, 1999; 2001 American Chemical Society, 123 5352-5353.

* cited by examiner

*Primary Examiner*—David Wu
*Assistant Examiner*—Rip A. Lee
(74) *Attorney, Agent, or Firm*—Barry D. Cash

(57) ABSTRACT

Olefins are polymerized by novel transition metal complexes of selected iminocarboxylate and iminoamido ligands, sometimes in the presence of cocatalysts such as alkylaluminum compounds or neutral Lewis acids. Olefins which may be (co)polymerized include ethylene, α-olefins, and olefins containing polar groups such as olefinic esters for example acrylate esters. Also described are certain "Zwitterionic" transition metal complexes as polymerization catalysts for making polar copolymers. The resulting polymers are useful as thermoplastics and elastomers.

11 Claims, No Drawings

POLYMERIZATION OF OLEFINS

CROSS-REFERENCE TO RELATED APPLICATION

This application claims priority under 35 U.S.C. §119 from U.S. National application Ser. No. 09/871,100 (filed May 31, 2001 now issued as U.S. Pat. No. 6,506,861); and U.S. Provisional Application Serial Nos. 60/208,087 (filed May 31, 2000), 60/211,601 (filed Jun. 15, 2000), and 60/214,036 (filed Jun. 23, 2000), the disclosures of each of which are hereby incorporated herein by reference.

FIELD OF THE INVENTION

Selected transition metal complexes of iminocarboxylate and iminoamido ligands, sometimes in the presence of certain cocatalysts, are catalysts for the (co)polymerization of olefins such as ethylene, α-olefins, and certain polar olefins such as olefinic esters. Preferred transition metals include nickel, titanium and zirconium. Also described are certain "Zwitterionic" transition metal complexes as polymerization catalysts for making polar copolymers.

TECHNICAL BACKGROUND

Olefins may be polymerized by a variety of transition metal containing catalysts, for example metallocene and Ziegler-Natta type catalysts. More recently, late transition metal containing polymerization catalysts have also been discovered, and among them are nickel and other transition metal containing catalysts in which the metal atom is complexed to a monoanionic and presumed bidentate ligand, see for instance WO9842664, WO9842665, U.S. Pat. No. 6,060,569, U.S. Pat. No. 6,174,975 and S. D. Ittel, et al., *Chem. Rev.*, vol. 100, p. 1169-1203 (2000) (and references cited therein). S. Y. Desjardins, et al., *J. Organometal. Chem.*, vol. 515, p. 233-243 (1996), ibid., vol. 544, p. 163-174 (1997), describe the oligomerization/polymerization of ethylene using nickel complexes of certain pyridine carboxylates.

U.S. Pat. No. 6,174,976 describes the use of certain neutral nickel complexes of ligands containing imino and carboxylate groups to polymerize hydrocarbon monoolefins.

In the following references, Zwitterionic nickel catalysts based on phosphine carboxylate ligands were utilized to carry out ethylene oligomerizations; however, polar monomers were not incorporated in any of the oligomers made with these systems: Komon, Z. J. A., et. al., *J. Am. Chem. Soc.*, 122, 1830-1831 (2000); Komon, Z. J. A., et. al., *J. Am. Chem. Soc.*, 122, 12379-12380 (2000).

Zwitterionic systems have been proposed in U.S. Pat. No. 6,103,658 and U.S. Pat. No. 6,200,925, but no polar monomers were incorporated in any of the polymers made with these systems.

All of the above publications are incorporated by reference herein for all purposes as if fully set forth.

None of these publications describes the complexes disclosed herein. Since polyolefins are important commercial materials, new catalysts for their manufacture are constantly being sought.

SUMMARY OF THE INVENTION

This invention concerns a process for the polymerization of olefins, comprising the step of contacting, under olefin polymerizing conditions, a monomer component comprising one or more of an olefin of the formula $H_2C=CHR^4$, a norbornene, a styrene, a cyclopentene or a polar olefin, especially an olefin of the formula $H_2C=CHR^4$ or a polar olefin of the formula $H_2C=CHR^5CO_2R^6$, with a transition metal complex of a ligand of the formula

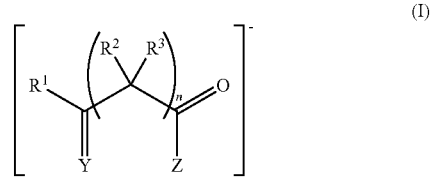

wherein:
Y is oxo, $NR^{12}$ or $PR^{12}$
Z is O, $NR^{13}$, S or $PR^{13}$;
each of $R^1$, $R^2$ and $R^3$ is independently hydrogen, hydrocarbyl, substituted hydrocarbyl or a functional group;
n is 0 or 1;
$R^4$ is hydrogen, alkyl or substituted alkyl;
$R^5$ is a covalent bond, alkylene or substituted alkylene;
$R^6$ is hydrogen, a metal cation, hydrocarbyl or substituted hydrocarbyl;
each $R^{12}$ is independently hydrogen, hydrocarbyl, substituted hydrocarbyl or a functional group;
each $R^{13}$ is independently hydrogen, hydrocarbyl, substituted hydrocarbyl or a functional group;
and provided that any two of $R^1$, $R^2$ and $R^3$ geminal or vicinal to one another taken together may form a ring.

In the above mentioned process, the transition metal complex of (I) may in and of itself be an active catalyst, or may be "activated" by contact with a cocatalyst/activator as further described below.

The present invention also concerns the ligand of the formula (I), transition metal complexes thereof, and polymerization catalyst components comprising these transition metal complexes.

This invention also concerns a process for the manufacture of a polar copolymer, wherein one or more hydrocarbon olefins, one or more polar olefins, and a polymerization catalyst system having a transition metal complex component containing a transition metal of groups 6-11 or a lanthanide metal, are contacted under polymerizing conditions to form said polar copolymer, wherein the transition metal complex component comprises a Zwitterionic complex.

These and other features and advantages of the present invention will be more readily understood by those of ordinary skill in the art from a reading of the following detailed description. It is to be appreciated that certain features of the invention which are, for clarity, described below in the context of separate embodiments, may also be provided in combination in a single embodiment. Conversely, various features of the invention which are, for brevity, described in the context of a single embodiment, may also be provided separately or in any subcombination.

DETAILED DESCRIPTION OF THE PREFERRED EMBODIMENTS

Herein, certain terms are used. Some of them are:

A "hydrocarbyl group" is a univalent group containing only carbon and hydrogen. As examples of hydrocarbyls may be mentioned unsubstituted alkyls, cycloalkyls and aryls. If not otherwise stated, it is preferred that hydrocarbyl groups (and alkyl groups) herein contain 1 to about 30 carbon atoms.

By "substituted hydrocarbyl" herein is meant a hydrocarbyl group that contains one or more substituent groups which are inert under the process conditions to which the compound containing these groups is subjected (e.g., an inert functional group, see below). The substituent groups also do not substantially detrimentally interfere with the polymerization process or operation of the polymerization catalyst system. If not otherwise stated, it is preferred that substituted hydrocarbyl groups herein contain 1 to about 30 carbon atoms. Included in the meaning of "substituted" are chains or rings containing one or more heteroatoms, such as nitrogen, oxygen and/or sulfur, and the free valence of the substituted hydrocarbyl may be to the heteroatom. In a substituted hydrocarbyl, all of the hydrogens may be substituted, as in trifluoromethyl.

By "(inert) functional group" herein is meant a group, other than hydrocarbyl or substituted hydrocarbyl, which is inert under the process conditions to which the compound containing the group is subjected. The functional groups also do not substantially deleteriously interfere with any process described herein that the compound in which they are present may take part in. Examples of functional groups include, for example, halo (fluoro, chloro, bromo and iodo), ether such as —$OR^{22}$ wherein $R^{22}$ is hydrocarbyl or substituted hydrocarbyl, silyl, substituted silyl, thioether and tertiary amino. In cases in which the functional group may be near a transition metal atom, the functional group alone should not coordinate to the metal atom more strongly than the groups in those compounds that are shown as coordinating to the metal atom, that is they should not displace the desired coordinating group.

By a "cocatalyst" or a "catalyst activator" is meant one or more compounds that react with a transition metal compound to form an activated catalyst species. One such catalyst activator is an "alkyl aluminum compound" which, herein, is meant a compound in which at least one alkyl group is bound to an aluminum atom. Other groups such as, for example, alkoxide, hydride and halogen may also be bound to aluminum atoms in the compound.

By "neutral Lewis base" is meant a compound, that is not an ion, which can act as a Lewis base. Examples of such compounds include ethers, amines, thioethers, olefins and organic nitriles.

By "neutral Lewis acid" is meant a compound, that is not an ion, which can act as a Lewis acid. Examples of such compounds include boranes, alkylaluminum compounds, aluminum halides and antimony [V] halides.

By "cationic Lewis acid" is meant a cation which can act as a Lewis acid. Examples of such cations are sodium and silver cations.

By an "empty coordination site" is meant a potential coordination site on a transition metal atom that does not have a ligand bound to it. Thus if an olefin molecule (such as ethylene) is in the proximity of the empty coordination site, the olefin molecule may coordinate to the metal atom.

By a "ligand into which an olefin molecule may insert between the ligand and a metal atom", or a "ligand that may add to an olefin", is meant a ligand coordinated to a metal atom which forms a bond (L—M) into which an olefin molecule (or a coordinated olefin molecule) may insert to start or continue a polymerization. For instance, with ethylene this may take the form of the reaction (wherein L is a ligand):

By a "ligand which may be displaced by an olefin" is meant a ligand coordinated to a transition metal which, when exposed to the olefin (such as ethylene), is displaced as the ligand by the olefin.

By a "monoanionic ligand" is meant a ligand with one negative charge.

By a "neutral ligand" is meant a ligand that is not charged.

"Alkyl group" and "substituted alkyl group" have their usual meaning (see above for substituted under substituted hydrocarbyl). Unless otherwise stated, alkyl groups and substituted alkyl groups preferably have 1 to about 30 carbon atoms.

By "aryl" is meant a monovalent aromatic group in which the free valence is to the carbon atom of an aromatic ring. An aryl may have one or more aromatic rings which may be fused, connected by single bonds or other groups.

By "substituted aryl" is meant a monovalent aromatic group substituted as set forth in the above definition of "substituted hydrocarbyl". Similar to an aryl, a substituted aryl may have one or more aromatic rings which may be fused, connected by single bonds or other groups; however, when the substituted aryl has a heteroaromatic ring, the free valence in the substituted aryl group can be to a heteroatom (such as nitrogen) of the heteroaromatic ring instead of a carbon.

By a "π-allyl group" is meant a monoanionic ligand comprised of 1 $sp^3$ and two $sp^2$ carbon atoms bound to a metal center in a delocalized $\eta^3$ fashion indicated by

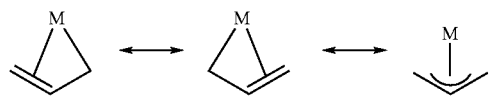

The three carbon atoms may be substituted with other hydrocarbyl groups or functional groups.

By a "styrene" herein is meant a compound of the formula

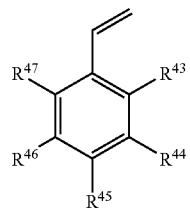

(XXXIV)

wherein $R^{43}$, $R^{44}$, $R^{45}$, $R^{46}$ and $R^{47}$ are each independently hydrogen, hydrocarbyl, substituted hydrocarbyl or a functional group, all of which are inert in the polymerization process. It is preferred that all of $R^{43}$, $R^{44}$, $R^{45}$, $R^{46}$ and $R^{47}$ are hydrogen. Styrene (itself) is a preferred styrene.

By a "norbornene" is meant ethylidene norbornene, dicyclopentadiene or a compound of the formula

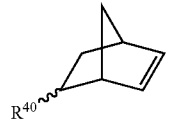

(XXXV)

wherein $R^{40}$ is hydrogen or hydrocarbyl containing 1 to 20 carbon atoms. It is preferred that $R^{40}$ is hydrogen or alkyl, more preferably hydrogen or n-alkyl, and especially preferably hydrogen. The norbornene may be substituted by one or more hydrocarbyl, substituted hydrocarbyl or functional groups in the $R^{40}$ or other positions, with the exception of the vinylic hydrogens, which remain. Norbornene (itself) is a preferred norbornene.

By a "cyclopentene" herein is meant cyclopentene or a substituted cyclopentene. Preferred cyclopentenes are cyclopentene, 1- or 3-methylcyclopentene and 1- or 3-ethylcyclopentene, and cyclopentylcyclopentene, and cyclopentene is more preferred.

By "$E_s$" is meant a parameter to quantify steric effects of various groupings, see R. W. Taft, Jr., *J. Am. Chem. Soc.*, vol. 74, p. 3120-3128 (1952), and M. S. Newman, *Steric Effects in Organic Chemistry*, John Wiley & Sons, New York, 1956, p. 598-603, which are both hereby included by reference. For the purposes herein, the $E_s$ values are those described for o-substituted benzoates in these publications. If the value of $E_s$ for a particular group is not known, it can be determined by methods described in these references.

By "aryl substituted in at least one position vicinal to the free bond of the aryl group," is meant the bond to one of the carbon atoms next to the free valence of the aryl group is something other than hydrogen. For example for a phenyl group, it would mean the 2 position of the phenyl group would have something other than hydrogen attached to it. A 1-naphthyl group already has something other than hydrogen attached to one of the vicinal carbon atoms at the fused ring junction, while a 2-napthyl group would have to be substituted in either the 1 or 3 positions to meet this limitation. A preferred aryl substituted in at least one position vicinal to the free bond of the aryl group is a phenyl group substituted in the 2 and 6 positions, and optionally in the other positions.

By a "polar (co)monomer" or "polar olefin" is meant an olefin which contains elements other than carbon and hydrogen. When copolymerized into a polymer the polymer is termed a "polar copolymer". Useful polar comonomers are found in U.S. Pat. No. 5,866,663, WO9905189, WO9909078 and WO9837110, and S. D. Ittel, et al., *Chem. Rev.*, vol. 100, p. 1169-1203(2000), all of which are incorporated by reference herein for all purposes as if fully set forth. Also included as a polar comonomer is CO (carbon monoxide).

By "under polymerization conditions" is meant the conditions for a polymerization that are usually used for the particular polymerization catalyst system being used. These conditions include paraneters such as pressure, temperature, catalyst and cocatalyst (if present) concentrations, the type of process such as batch, semibatch, continuous, gas phase, solution or liquid slurry etc., except as modified by conditions specified or suggested herein. Conditions normally done or used with the particular polymerization catalyst system, such as the use of hydrogen for polymer molecular weight control, are also considered "under polymerization conditions". Other polymerization conditions such as presence of hydrogen for molecular weight control, other polymerization catalysts, etc., are applicable with this polymerization process and may be found in the references cited and incorporated herein.

The polymerizations herein are carried out by a transition metal complex of anion (I). In (I), and in all complexes and compounds containing (I) or its parent conjugate acid, it is preferred that:

Y is oxo or $NR^{12}$;

Z is O or $NR^{13}$;

n is 0; and/or $R^1$ is hydrocarbyl or hydrogen, more preferably hydrogen or alkyl; especially preferably alkyl, and particularly methyl; and/or $R^2$ and $R^3$, when present (n is 1), are each independently hydrocarbyl or hydrogen, more preferably hydrogen or alkyl; especially preferably methyl or hydrogen; and/or $R^{12}$ and $R^{13}$ are each independently hydrocarbyl or substituted hydrocarbyl, more preferably aryl, substituted aryl or alkyl; more preferably 9-phenanthryl, 1- or 2-naphthyl or substituted 1- or 2-naphthyl, or

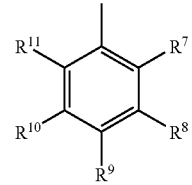

(II)

wherein each of $R^7$, $R^8$, $R^9$, $R^{10}$ and $R^{11}$ is independently hydrogen, hydrocarbyl, substituted hydrocarbyl or a functional group. In another preferred form, one or both of $R^{12}$ and/or $R^{13}$ are aryl or substituted aryl in which at least one bond vicinal to the free bond of the aromatic group is substituted, or $R^{12}$ and/or $R^{13}$ are a group with an $E_s$ of less than about −1.0, more preferably less than about −1.5, or both.

In (I) and its complexes, more specific preferred combinations are:

when Y is O (oxo) and Z is $NR^{13}$; $R^1$ is hydrogen or hydrocarbyl, more preferably alkyl or aryl; $R^{13}$ is hydrocarbyl or substituted hydrocarbyl having an $E_s$ of less than −1.0, or aryl or substituted aryl in which at least one bond vicinal to the free bond of the aromatic group is substituted, more preferably 2,6-disubstituted phenyl (optionally with one or more of the other positions on the phenyl group substituted); or when Y is $NR^{12}$ and Z is $NR^{13}$; $R^1$ is hydrogen or hydrocarbyl, more preferably alkyl or aryl; one or both of $R^{12}$ and $R^{13}$ is hydrocarbyl or substituted hydrocarbyl having an $E_s$ of less than −1.0, or aryl or substituted aryl in which at least one bond vicinal to the free bond of the aromatic group is substituted, more preferably $R^{12}$ is 2,6-disubstituted phenyl (optionally with one or more of the other positions on the phenyl group substituted).

In (II) it is preferred that one or both of $R^7$ and $R^{11}$ are other than hydrogen, more preferably hydrocarbyl or a functional group, especially preferably alkyl containing 1 to 6 carbon atoms, aryl (such as pehnyl or a hydrocarbyl substituted phenyl such as 4-t-butylphenyl), halo or alkoxy.

A specific preferred ligand (I) (and its corresponding conjugate acid and transition metal complexes) include one in which $R^1$ is methyl; n is 0; Y is $NR^{12}$, $R^{12}$ is (II); $R^8$, $R^9$ and $R^{10}$ are hydrogen; and $R^7$ and $R^{11}$ are isopropyl.

In transition metal complexes of (I), useful transition metals include Group 3-11 (IUPAC) transition metals and lanthanide metals such as Ni, Pd, Pt, Fe, Co, Ti, Zr, V, Hf, Cr, Mn, Ru, Rh, Re, Os, Ir, Cu and the rare earths (lanthanides). Preferred transition metals are Ni, Zr, Ti, Fe, Co and Cu, and Ni, Ti and Zr are more preferred. When Ni, Fe or Co are the transition metals a preferred oxidation state is [II], when Zr or Ti are the transition metals a preferred oxidation state is [IV], and when Cu is the transition metal preferred oxidation states are [I] and [II].

The complexes of the transition metals may contain one or two of the ligands (I) per transition metal atom, depending on the particular transition metal. For example early transition metals which may be pentacoordinate or hexacoordinate may have one or two ligands per metal atom respectively, as exemplified in the structures

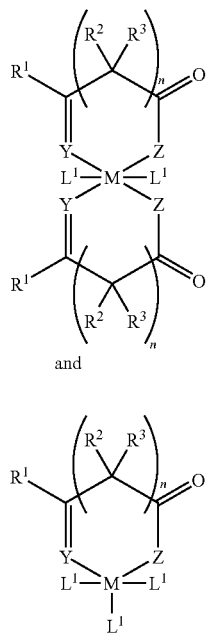

(III)

and

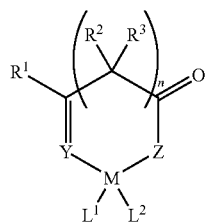

(IV)

wherein, for example, M (the transition metal) may be Ti[IV] or Zr[IV], and each $L^1$ is a monodentate, monoanionic ligand such as chloride.

For some late transition metals such as Ni which tend to be tetracoordinate, a typical complex may be

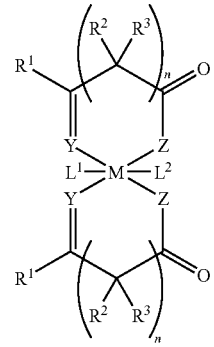

(V)

wherein, for example, M (the transition metal) is Ni[II], $L^1$ is a monoanionic, monodentate ligand such as chloride or methyl, and $L^2$ is a monodentate neutral ligand such as acetonitrile, or an empty coordination site, or $L^1$ and $L^2$ taken together are a monoanionic, bidentate ligand such as a π-allyl group.

Although the complexes of (I) are drawn with (I) as a bidentate ligand it is to be understood that this is for convenience only in representing these complexes, and any transition metal complex of (I), whether (I) is monodentate, bidentate, etc., is included within the meaning of a complex of (I).

It is believed that, in the active polymerization catalyst species herein, at least one of the ligands (e.g., $L^1$) is preferably a ligand that may add to an olefin. It is further believed that, in the late transition metal active polymerization catalyst species herein, another of the ligands (e.g., $L^2$) is a neutral ligand which may be displaced by an olefin, or an empty coordination site, or the olefin itself. Examples of ligands that may add to an olefin include hydrocarbyl and substituted hydrocarbyl (especially phenyl and alkyl, and particularly methyl), hydride and acyl. Examples of ligands which may be displaced by ethylene include phosphines (such as triphenylphosphine), nitriles (such as acetonitrile), ethers (such as ethyl ether), pyridine and tertiary alkylamines (such as TMEDA (N,N,N',N'-tetramethylethyenediamine)).

Herein, as indicated above, ligands that may add to an olefin can be $L^1$, and ligands which may be displaced by ethylene may be $L^2$, as for instance shown in (V) and (VI).

(VI)

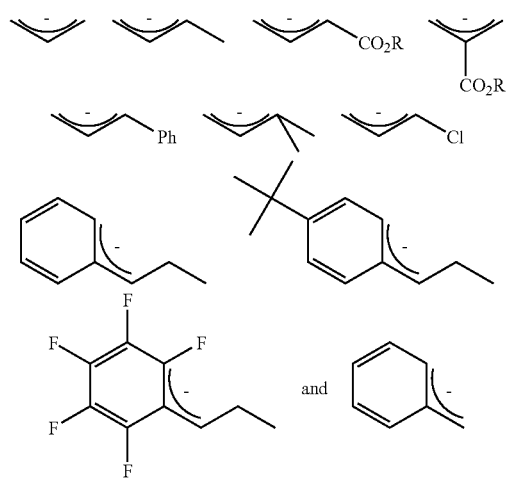

Particularly at the beginning of the polymerization, $L^1$ and $L^2$ taken together may be a bidentate monoanionic ligand into which an olefin molecule (such as ethylene) may insert between that ligand and the transition metal atom, such as π-allyl- or π-benzyl-type ligands such as wherein R is hydrocarbyl. In this instance, sometimes it may be necessary to add a neutral Lewis acid cocatalyst such as triphenylborane or tris(pentafluorophenyl)borane to initiate the polymerization, see below and for instance U.S. Pat. No. 5,880,241, which is incorporated by reference herein for all purposes as if fully set forth. For a summary of which ligands olefins may insert into (between the ligand and transition metal atom) see for instance J. P. Collman, et al., *Principles and Applications of Organotransition Metal Chemistry*, University Science Books, Mill Valley, Calif., 1987.

If for instance $L^1$ is not a ligand into which ethylene may insert between it and the transition metal atom, it may be possible to add a cocatalyst that may convert $L^1$ into a ligand which will undergo such an insertion. Thus if $L^1$ is halo such as chloride or bromide, carboxylate or acetylacetonate, it may be converted to hydrocarbyl such as alkyl by use of a suitable alkylating agent such as an alkylaluminum compound, a Grignard reagent or an alkyllithium compound. It may be converted to hydride by used of a compound such as sodium borohydride.

It is preferred that the alkylating compound (cocatalyst or activator) be both an alkylating compound and a neutral Lewis acid. A preferred cocatalyst is an alkylaluminum compound, and useful alkylaluminum compounds include trialkylaluminum compounds such as triethylaluminum, trimethylaluminum and tri-i-butylaluminum, alkyl aluminum halides such as diethylaluminum chloride and ethylaluminum dichloride, and aluminoxanes such as methylaluminoxane. Alternatively, a combination of an alkylating agent (which may be a relatively weak Lewis acid) and another stronger neutral Lewis acid may be present as the cocatalyst(s). Even if $L^1$ is already a ligand into which ethylene may insert, it may be advantageous to have a neutral Lewis acid present as a cocatalyst. It is preferred when a late transition metal, especially Ni, is used, that a neutral Lewis acid be present, especially at lower process temperatures.

Once the polymerization has started on a particular transition metal site, the ligand into which an olefin may insert will often be a ligand which is in fact the growing polymer chain whose composition will be the monomer(s) being polymerized and the end group the original $L^1$ which the first olefin molecule inserted into (between the ligand and metal). This polymer ligand may be represented by the group —$PL^1$, wherein P is a divalent "polymeric" (but which may have only one or few repeat units at times), and will be understood to contain one or more repeat units derived from the monomer (s) used. If chain transfer occurs, for instance by β-hydride elimination to form a hydride ligand on the transition metal, the end group of the next polymer chain will be hydrogen.

A general formula for a transition metal complex useful herein can be written as $(L^1)_x(L^2)_y(L^3)_zM$ (VIII) wherein $L^1$ and $L^2$ are as defined above, $L^3$ is (I), z is 1 or 2, M is a transition metal of oxidation state q, y is an integer of 1 to 3, and x=(q−z). $L^1$ and $L^2$ may have the variations mentioned above, and when $L^1$ and $L^2$ are the indicated groups, the transition metal compound may inherently be an active polymerization catalyst. Table 1 gives preferred transition metal compounds (VIII). Preferred ligands $L^3$ for these compounds are as described above.

TABLE 1

| M | q | $L^1$ | x | $L^2$ | y | z |
|---|---|---|---|---|---|---|
| Ni | 2 | π-allyl[a] | 1[a] | π-allyl[a] | 1[a] | 1 |
| Zr | 4 | Cl | 2 | — | 0 | 2 |
| Zr | 4 | Cl | 3 | — | 0 | 1 |
| Ti | 4 | Cl | 2 | — | 0 | 2 |
| Ti | 4 | Cl | 3 | — | 0 | 1 |

[a]$L^1$ and $L^2$ combined in a single π-allyl-type group.

Included within the meaning of the transition metal complexes of (I) herein are Lewis acid adducts of such complexes. By this is meant an adduct formed between the transition metal complex of (I) and a neutral Lewis acid. The structures of such adduct complexes may often be written as

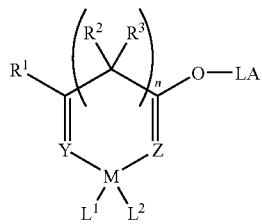

(XI)

wherein $R^1$, $R^2$, $R^3$, n, Z, Y, M, $L^1$ and $L^2$ are as defined above, and LA (by itself) is a neutral Lewis acid. Preferably the metal is a late transition metal of Groups 6-11, more preferably Groups 8-11. Suitable neutral Lewis acids include boranes such as tris(pentafluorophenyl)borane, triphenylborane, and aluminanes such as trihydrocarbylaluminum, especially trialkylaluminum (for example triethylaluminum), and others which can coordinate with the transition metal complex.

More generally (with other suitable ligands as well, see below) such complexes, called herein Zwitterionic complexes, are particularly useful in the copolymerization of a hydrocarbon olefin (such as ethylene) and a polar comonomer, especially vinyl polar comonomers (in a vinyl polar comonomer the polar group is attached directly to a vinylic carbon atom, as in acrylic monomers), particularly when using a complex of a late transition metal of Groups 8-11. Preferred metals are Pd and Ni, and Ni is especially preferred. Suitable neutral Lewis acids include tris(pentafluorophenyl)borane, triphenylborane, trihydrocarbylaluminum, especially trialkylaluminum (for example triethylaluminum), and others which can coordinate with the transition metal complex. Preferably the Lewis acid should not react with any other component of the polymerization catalyst system, for example not contain "active" halogen groups which may react with an alkylaluminum compound, if an alkylaluminum compound is present in the polymerization process. The Lewis acid is coordinated to a Lewis base which is present in the ligand of the metal complex. Therefore, the Lewis acid may be removed from ligand (metal complex) by addition of a Lewis base which is a stronger Lewis base than the group on the ligand to which the Lewis acid is coordinated (bound). Lewis acid in this instance does not mean a Lewis acid which is relatively permanently covalently bound to the ligands, for example —$B(aryl)_2$ where the boron is covalently bound to a carbon atom of the ligand.

When using Zwitterionic materials to form polar comonomers, preferred hydrocarbon olefins are ethylene and $H_2C=CHR^4$, wherein $R^4$ is alkyl or substituted alkyl, preferably n-alkylene, and ethylene is especially preferred. A preferred polar olefin is $H_2C=CHR^5CO_2R^6$, particularly wherein $R^5$ is a covalent bond, and $R^6$ is hydrocarbyl or substituted hydrocarbyl.

When the transition metal complex in the Zwitterionic compound is a Ni complex, it is preferred that the Ni atom be coordinated to a neutral bidentate ligand or a monoanionic bidentate ligand. In order to form a Zwitterionic compound using a complex of any transition metal with any ligand, the ligand will normally contain a group which is a Lewis base. The combination of this Lewis base group and neutral Lewis acid chosen will normally have a large enough difference in Lewis acidity and basicity to form a complex. For example a group which is a weak Lewis base may form a Zwitterionic compound with a strong Lewis acid, and vice versa.

Generally speaking a Zwitterionic complex will be detectable using any number of methods. For instance it may be isolable as the Zwitterionic complex, and the structure proven by various methods such as X-ray diffraction or various spectroscopic methods such as NMR or infrared spectroscopy. Its presence may also be shown in solution, such as by ultraviolet, infrared or NMR spectroscopy. If any of these or other methods shows the presence of the Zwitterionic compound, it is deemed this complex is an active polymerization catalyst.

In any of the polymerization processes herein in which a polar comonomer is copolymerized, and in any formation of any polar copolymer, it is preferred that the molar ratio of the total of the polar comonomers present to any added Lewis acid is at least 2:1, preferably at least 10:1. Polar comonomers, such acrylic-type monomers, have been copolymerized in certain situations by destroying their Lewis basic (or coordinating) character by reacting them with a Lewis acid, to form a Lewis acid "salt" of the polar comonomer. While this may often help to form the polar copolymer, later removal of the stoichiometric amount (relative to the polar comonomer) of Lewis acid is difficult and expensive.

It is also noted that when Zwitterionic complexes are used as part of the olefin polymerization catalyst system, even in the polymerization of hydrocarbon olefins (no polar olefins present), such as ethylene, there is an improvement in the polymerization, such as improved polymer productivity and/or longer catalyst life.

In one preferred form of the present Zwitterionic compounds, the Lewis acid which complexes to the ligand in the transition metal complex preferably is not in a position to readily interact with any polar groups on the polar copolymer which is forming, particularly polar groups very close to the metal atom on the polymerizing polymer chain. This is particularly preferred with Ni complexes.

Dreiding Stereomodels (Manufactured by Büchi Laboratory-Techniques, Ltd., Switzerland, and available in the USA from Aldrich Chemical Company or other sources. The Normal Set, Aldrich Catalog Number Z24, 787-1 and the Porphyrin Set, Aldrich Catalog Number Z25, 644-7, together provide the parts required for this purpose) are a useful tool to understand the geometries of various catalytic complexes. They provide very precise bond distances and angles while maintaining all of the flexibility normally associated with atom-atom bonds. They are available with the nickel, carbon, nitrogen, oxygen, phosphorus, sulfur and all other atoms necessary for building all of the ligands and complexes discussed in this case. They also come with a convenient ruler to measure distance between atom centers in Ångstroms. They are useful to determine the potential for interaction between the polar functionality on the growing polymer chain and any Lewis acidic site in the complex. Through rotation about the Ni—C bond and any other C—C bonds in the polymer chain bound to the nickel center, the polar functionality is able to sweep out a conical volume of space. If there is any available Lewis acidic site within that space (which may also rotate into that space), it is presumed that there can be a bonding interaction with that Lewis acidic site which would compete in an equilibrium with the nickel center for the lone pair electrons on the polar functionality. The potential for interaction may be determined through the following construct.

Starting with a square planar nickel atom, the complex is constructed by binding the ligand to two of the adjacent coordination sites on nickel. A carbon atom is placed at a third site on nickel. The fourth coordination site on nickel is occupied by X, and A represents a ligand or a vacant coordination site.

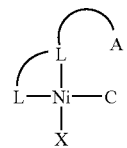

A solid cone is defined by the angle, $\theta$, and the distance (in Å), $\lambda$, in the manner shown, with the axis of the cone along the nickel-carbon bond. The maximum value possible for $\theta$ is 180°.

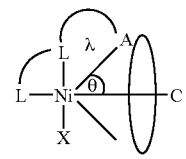

The conical volume of space through which the polar functionality attached to the growing polymer chain may sweep by means of rotation of the Ni—C and C—C bonds is determined through use of the models. This cone is the Lewis Acid Interaction Cone or LAIC. The angle increases for each additional carbon atom located between the nickel center and the polar functionality. For instance, in the case of methyl acrylate, $\theta$ varies from 65 to 120° in going from one to three carbon atoms between the nickel center and the carbonyl functionality.

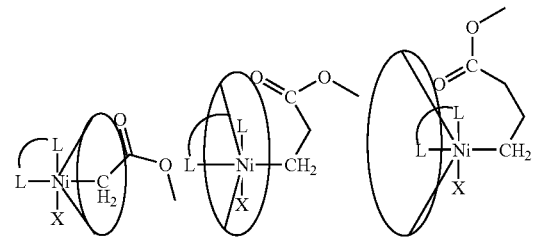

| $\theta =$ | 70 | 100 | 120° |

These are taken herein as typical values of the LAIC for a variety of commercially important polar olefins. Any catalyst complex having a Lewis acidic atom whose atomic center is within the LAIC may bond to the electron pair available on the polar functionality through said Lewis acid. On the other hand, the Lewis acid in

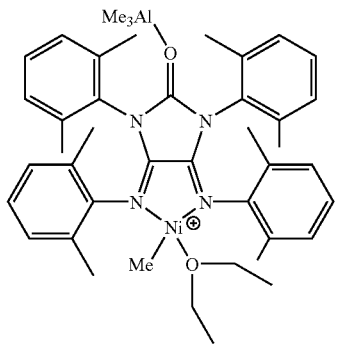

is well outside the LAIC even at θ=130° (and is preferred herein) and will not be involved in binding to the Lewis-basic electron pair of the polar functionality. To be one type of preferred Lewis acid herein, the LAIC should be greater than 130°, preferably greater than about 150°.

The volume swept out by the rotating carbonyl is also limited in its distance, λ, from the nickel center. It may not come closer to nickel than the bonding distance of just over 2 Å. Maximizing the distance from the metal center, one observes 4.5, 5.0 and 6.5 Å, respectively for one, two and three carbons between nickel and the carbonyl group. These distances impose a further constraint upon the position of the Lewis acid, but the distance from the metal center is seldom a limitation in the construction of ligands.

When Z in (I) is O, the ligand may be made by reaction of an amine $R^{12}NH_2$ with a metal salt, preferably an alkali metal salt, of an appropriate carboxylic acid

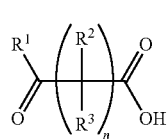

(VII)

wherein $R^1$, $R^2$, $R^3$, $R^{12}$ and n are as defined above. This reaction yields the ligand (I) as its (alkali) metal salt. This salt may then be reacted with an appropriate transition metal compound to form a complex of (I) and the transition metal. For example for early transition metals this may simply be a halide such as $TiCl_4$ or $ZrCl_4$. For late transition metal complexes it may also be a halide such as $NiBr_2$, $(COD)NiBr_2$ (COD is 1,5-cyclooctadiene) or the nickel allyl chloride dimer. In another method of forming the transition metal complex with late transition metals the conjugate acid of (I) can be used to protonate a dialkyl transition metal complex such as $(TMEDA)Ni(CH_3)_2$ (TMEDA is N,N,N',N'-tetramethylethylenediamine) to form the desired complex. As noted above, if the transition metal compound is not at this point an active polymerization catalyst by itself, appropriate cocatalysts may be added.

When Z is N, the organometallic compound may be made by the following scheme, illustrated for Ni. If n is 1, an analogous starting material may be used. Complexes of other metals can be made by methods generally described in the immediately preceding paragraph.

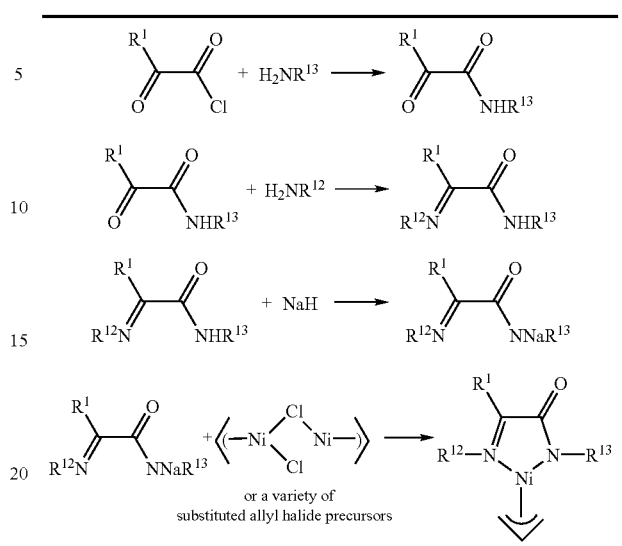

or a variety of substituted allyl halide precursors

If Z is S or $PR^{13}$, and/or Y is O or $PR^{12}$, analogous starting materials and methods may be used to make the ligand and the transition metal compound.

Preferred monomers herein are hydrocarbon monomers of the formula $H_2C=CHR^4$, or polar olefins of the formula $H_2C=CHR^5CO_2R^6$, and combinations thereof. A particularly preferred hydrocarbon monomer is ethylene ($R^4$ is hydrogen). Another preferred hydrocarbon monomer is an alpha-olefin ($R^4$ is alkyl), particularly when $R^4$ is an n-alkyl containing 1 to 14 carbon atoms, and especially when $R^4$ is methyl (propylene). $R^6$ may be a metal or onium cation (such as ammonium), in which case the polar olefin would be a carboxylate salt. Preferred cations include alkali metal cations and ammonium. For the polar olefins, it is preferred that $R^6$ is alkyl, especially alkyl containing 1 to 4 carbon atoms, and/or $R^5$ is a covalent bond or $—(CH_2)_r—$ wherein r is 1 to 19. A particularly preferred combination of monomers is ethylene with one or more alpha-olefins, polar olefins and/or a cyclopentene, especially ethylene with one or more polar olefins. In all instances the corresponding copolymers are formed.

When a polar olefin is present as a (co)monomer, it is preferred that the transition metal is a late transition metal, particularly Ni, Pd or Cu, more preferably Ni. Useful polar olefins include those of the general formula $H_2C=CHR^{15}E$, wherein $R^{15}$ is alkylene, alkylidene or a covalent bond, especially $—(CH_2)_x—$ wherein x is 0 or an integer of 1 to 20 and E is a polar group. Useful polar groups E include $—CO_2R^{14}$, $—CO_2H$, $—C(O)NR^{14}_2$ and $—OR^{14}$, and $—CO_2R^{14}$ and $—OR^{14}$ are more preferred, wherein each $R^{14}$ is hydrogen, hydrocarbyl or substituted hydrocarbyl, preferably alkyl or substituted alkyl. For any olefin other than a norbornene, cyclopentene and/or a styrene, it is preferred that it be copolymerized with ethylene. An especially preferred olefin is ethylene (alone). Typically CO and polar comonomers will be used with a hydrocarbon olefin such as ethylene to form a copolymer.

When in the polymerization process and in the metal complex Z is O and M is Ni, it is preferred that the olefin(s) to be polymerized comprise at least one polar olefin, except when said complex is further complexed with a Lewis acid (see above). Also when M is Ni in the transition metal complex and Y is $NR^{12}$, it is preferred that Z is not O.

In the polymerization process herein, the temperature at which the polymerization is carried out is about −100° C. to about +200° C., preferably about −60° C. to about 150° C., more preferably about −20° C. to about 100° C. The pressure of a gaseous olefin such as ethylene at which the polymerization is carried out is not critical, atmospheric pressure to about 275 MPa being a suitable range. Liquid olefins may be present in virtually any concentration although the polymerization may be slowed down by high concentrations of polar olefins.

When a polar comonomer and ethylene are present, and a Ni complex (Zwitterionic or not) is used in the polymerization catalyst system, it is preferred that the polymerization process be run at a temperature of about 50° C. or more, more preferably 60° C. to about 170° C., and an ethylene partial pressure of at least about 700 kPa. More preferably the temperature range is about 80° C. to about 140° C. and/or a lower ethylene pressure is about 5.0 MPa or more, and/or a preferred upper limit on ethylene pressure is about 200 MPa, especially preferably about 20 MPa. The polymerization process herein may be run in the presence of various liquids, particularly aprotic organic liquids. The catalyst system, olefinic monomer(s), and/or polymer may be soluble or insoluble in these liquids, but obviously these liquids should not prevent the polymerization from occurring. Suitable liquids include alkanes, cycloalkanes, selected halogenated hydrocarbons, and aromatic hydrocarbons. Specific useful solvents include hexane, toluene, benzene, methylene chloride, 1,2,4-trichlorobenzene and p-xylene.

The olefin polymerizations herein may also initially be carried out in the "solid state" by, for instance, supporting the transition metal compound on a substrate such as silica or alumina, activating if necessary it with one or more cocatalysts and contacting it with the olefin(s). Alternatively, the support may first be contacted (reacted) with cocatalysts (if needed) such as an alkylaluminum compound, and then contacted with an appropriate transition metal compound. The support may also be able to take the place of a Lewis or Bronsted acid, for instance an acidic clay such as montmorillonite, if needed. These "heterogeneous" catalysts may be used to catalyze polymerization in the gas phase or the liquid phase. By gas phase is meant that a gaseous olefin is transported to contact with the catalyst particle. For the copolymerization of polar olefins using supported catalysts, especially in a liquid medium, a preferred case is when the ligand is covalently attached to the support, which helps prevent leaching of the transition metal complex from the support.

In all of the polymerization processes described herein oligomers and polymers of olefins are made. They may range in molecular weight from oligomeric POs (polyolefins), to lower molecular weight oils and waxes, to higher molecular weight POs. One preferred product is a PO with a degree of polymerization (DP) of about 10 or more, preferably about 40 or more. By "DP" is meant the average number of repeat units in a PO molecule.

Depending on their properties, the POs made by the processes described herein are useful in many ways. For instance if they are thermoplastics, they may be used as molding resins, for extrusion, films, etc. If they are elastomeric, they may be used as elastomers. If they contain functionalized monomers such as acrylate esters, they are useful for other purposes, see for instance previously incorporated U.S. Pat. No. 5,880,241.

It is believed that the late transition metal (such as Ni) containing catalysts used herein often give polymers which have unusual branching patterns, see for instance previously incorporated U.S. Pat. No. 5,880,241 and Z. Guan, et al., Science, vol. 283 p. 2059-2062 (1999). On the other hand, early transition metal (such as Ti and Zr) containing catalysts usually give polymers with more conventional branching, such as those made by Ziegler-Natta or metallocene polymerization catalysts.

Depending on the process conditions used and the polymerization catalyst system chosen, the POs may have varying properties. Some of the properties that may change are molecular weight and molecular weight distribution, crystallinity, melting point, and glass transition temperature. Except for molecular weight and molecular weight distribution, branching can affect all the other properties mentioned, and branching may be varied (using the same nickel compound) using methods described in previously incorporated U.S. Pat. No. 5,880,241.

It is known that blends of distinct polymers, that vary for instance in the properties listed above, may have advantageous properties compared to "single" polymers. For instance it is known that polymers with broad or bimodal molecular weight distributions may be melt processed (be shaped) more easily than narrower molecular weight distribution polymers. Thermoplastics such as crystalline polymers may often be toughened by blending with elastomeric polymers.

Therefore, methods of producing polymers which inherently produce polymer blends are useful especially if a later separate (and expensive) polymer mixing step can be avoided. However in such polymerizations one should be aware that two different catalysts may interfere with one another, or interact in such a way as to give a single polymer.

In such a process the transition metal containing polymerization catalyst disclosed herein can be termed the first active polymerization catalyst. A second active polymerization catalyst (and optionally one or more others) is used in conjunction with the first active polymerization catalyst. The second active polymerization catalyst may be another late transition metal catalyst, for example as described in previously incorporated U.S. Pat. No. 5,880,241, U.S. Pat. No. 6,060,569, U.S. Pat. No. 6,174,795 and S. D. Ittel, et al., Chem. Rev., vol. 100, p. 1169-1203 (2000) (and references cited therein), as well as U.S. Pat. No. 5,714,556 and U.S. Pat. No. 5,955,555 which are also incorporated by reference herein as if fully set forth. Other useful types of catalysts may also be used for the second active polymerization catalyst. For instance so-called Ziegler-Natta and/or metallocene-type catalysts may also be used. These types of catalysts are well known in the polyolefin field, see for instance Angew. Chem., Int. Ed. Engl., vol. 34, p. 1143-1170 (1995), EP-A-0416815 and U.S. Pat. No. 5,198,401 for information about metallocene-type catalysts, and J. Boor Jr., Ziegler-Natta Catalysts and Polymerizations, Academic Press, New York, 1979 for information about Ziegler-Natta-type catalysts, all of which are hereby included by reference. Many of the useful polymerization conditions for all of these types of catalysts and the first active polymerization catalysts coincide, so conditions for the polymerizations with first and second active polymerization catalysts are easily accessible. Oftentimes the "co-catalyst" or "activator" is needed for metallocene or Ziegler-Natta-type polymerizations. In many instances the same compound, such as an alkylaluminum compound, may be used as an "activator" for some or all of these various polymerization catalysts.

In one preferred process described herein the first olefin(s) (olefin(s) polymerized by the first active polymerization catalyst) and second olefin(s) (the monomer(s) polymerized by the second active polymerization catalyst) are identical. The second olefin may also be a single olefin or a mixture of olefins to make a copolymer.

In some processes herein the first active polymerization catalyst polymerizes one or more olefins, a monomer that may not be polymerized by said second active polymerization catalyst, and/or vice versa. In that instance two chemically distinct polymers may be produced. In another scenario two monomers would be present, with one polymerization catalyst producing a copolymer, and the other polymerization catalyst producing a homopolymer.

Likewise, conditions for such polymerizations, using catalysts of the second active polymerization type, will also be found in the appropriate above mentioned references.

Two chemically different active polymerization catalysts are used in this polymerization process. The first active polymerization catalyst is described in detail above. The second active polymerization catalyst may also meet the limitations of the first active polymerization catalyst, but must be chemically distinct. For instance, it may utilize a different ligand that differs in structure between the first and second active polymerization catalysts. In one preferred process, the ligand type and the metal are the same, but the ligands differ in their substituents.

Included within the definition of two active polymerization catalysts are systems in which a single polymerization catalyst is added together with another ligand, preferably the same type of ligand, which can displace the original ligand coordinated to the metal of the original active polymerization catalyst, to produce in situ two different polymerization catalysts.

The molar ratio of the first active polymerization catalyst to the second active polymerization catalyst used will depend on the ratio of polymer from each catalyst desired, and the relative rate of polymerization of each catalyst under the process conditions. For instance, if one wanted to prepare a "toughened" thermoplastic polyethylene that contained 80% crystalline polyethylene and 20% rubbery polyethylene, and the rates of polymerization of the two catalysts were equal, then one would use a 4:1 molar ratio of the catalyst that gave crystalline polyethylene to the catalyst that gave rubbery polyethylene. More than two active polymerization catalysts may also be used if the desired product is to contain more than two different types of polymer.

The polymers made by the first active polymerization catalyst and the second active polymerization catalyst may be made in sequence, i.e., a polymerization with one (either first or second) of the catalysts followed by a polymerization with the other catalyst, as by using two polymerization vessels in series. However it is preferred to carry out the polymerization using the first and second active polymerization catalysts in the same vessel(s), i.e., simultaneously. This is possible because in most instances the first and second active polymerization catalysts are compatible with each other, and they produce their distinctive polymers in the other catalyst's presence. Any of the processes applicable to the individual catalysts may be used in this polymerization process with 2 or more catalysts, i.e., gas phase, liquid phase, continuous, etc.

The polymers produced by this process may vary in molecular weight and/or molecular weight distribution and/or melting point and/or level of crystallinity, and/or glass transition temperature and/or other factors. The polymers produced are useful as molding and extrusion resins and in films as for packaging. They may have advantages such as improved melt processing, toughness and improved low temperature properties.

Catalyst components which include transition metal complexes of (I), with or without other materials such as one or more cocatalysts and/or other polymerization catalysts are also disclosed herein. For example, such a catalyst component could include the Ni complex supported on a support such as alumina, silica, a polymer, magnesium chloride, sodium chloride, etc., with or without other components being present. It may simply be a solution of the complex, or a slurry of the complex in a liquid, with or without a support being present.

Hydrogen or other chain transfer agents such as silanes (for example trimethylsilane or triethylsilane) may be used to lower the molecular weight of polyolefin produced in the polymerization process herein. It is preferred that the amount of hydrogen present be about 0.01 to about 50 mole percent of the olefin present, preferably about 1 to about 20 mole percent. The relative concentrations of a gaseous olefin such as ethylene and hydrogen may be regulated by varying their relative partial pressures.

In the Examples except where noted, all pressures are gauge pressures. In the Examples the following abbreviations are used:

$\Delta H_f$—heat of fusion in J/g
Am—amyl
Ar—aryl
BAF—$B(3,5-C_6H_3-(CF_3)_2)_4^-$
BArF—$B(C_6F_5)_4^-$
BHT—2,6-di-t-butyl-4-methylphenol
BQ—1,4-benzoquinone
Bu—butyl
$Bu_2O$—dibutyl ether
CB—chlorobenzene
Cmpd—compound
Cy—cyclohexyl
DMSO—dimethylsulfoxide
DSC—differential scanning calorimetry
E—ethylene
E-10-U—ethyl 10-undecylenate
EG—end-group, refers to the ester group of the acrylate being located in an unsaturated end group of the ethylene copolymer
EGPEA—2-phenoxyethyl acrylate
Eoc—end-of-chain
Equiv—equivalent
Et—ethyl
$Et_2O$—diethyl ether
GPC—gel permeation chromatography
HA—hexyl acrylate
Hex—hexyl
IC—in-chain, refers to the ester group of the acrylate being bound to the main-chain of the ethylene copolymer
Incorp—incorporation
i-Pr—i-propyl
LA—Lewis acid
M.W.—molecular weight
MA—methyl acrylate
Me—methyl
MeOH—methanol
MI—melt index
Mn—number average molecular weight
Mp—peak average molecular weight
Mw—weight average molecular weight
Nd—not determined
PDI—polydispersity; Mw/Mn
PE—polyethylene
Ph—phenyl
PMAO—polymethylaluminoxane
Press—pressure
RB—round-bottomed
RI—refractive index
RT or Rt—room temperature
t-Bu—t-butyl
TCB—1,2,4-trichlorobenzene
Temp—temperature
THF—tetrahydrofuran
TO—Number of turnovers per metal center=(moles monomer consumed, as determined by the weight of the isolated polymer or oligomers) divided by (moles catalyst)
TON—turnovers, moles of monomer (olefin) polymerized per mole of transition metal present
Total Me—total number of methyl groups per 1000 methylene groups as determined by 1H or 13C NMR analysis
UV—ultraviolet All operations related to the ligand/catalyst syntheses were performed in a nitrogen drybox or using a Schlenk line with nitrogen protection. Anhydrous solvents were used. Solvents were distilled from drying agents under nitrogen using standard procedures, for instance THF from sodium benzophenone ketyl. Ni[II] allyl chloride was prepared according to the literature (*Angew. Chem. Int. Ed. Engl.*, vol. 5, p. 151-266 (1966)). NMR spectra were recorded using a Bruker 500 MHz spectrometer.

The following transition metal compounds were made:

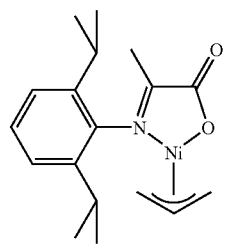

1

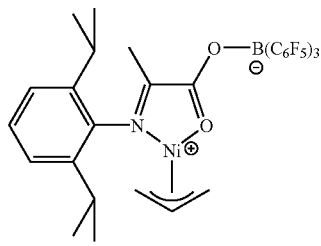

2

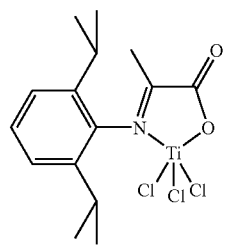

3

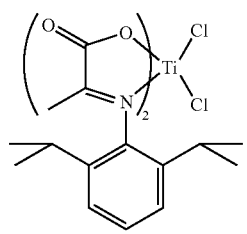

4

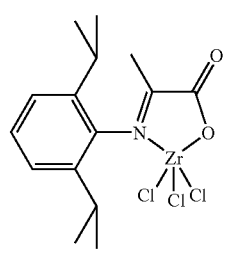

5

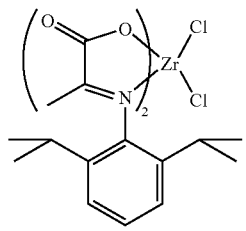

6

EXAMPLE 1

Synthesis of A

In a 300 mL RB flask, 5.000 g (0.04545 mole) sodium pyruvate and 8.059 g (0.04545 mole) 2,6-diisopropylaniline were mixed with 150 mL methanol, together with 5 drops of formic acid (96%). The mixture was allowed to stir at RT for 3 d. Some white solid (~1 g, possibly unreacted sodium pyruvate) remained and it was filtered off. The resulting solution was evaporated to dryness. The resulting mixture was dissolved in 80 mL methanol, followed by addition of 100 mL hexanes and 60 mL THF. A small amount of white precipitate formed. The mixture was cooled to −40° C. and then was filtered cold, followed by cold hexanes wash. The filtrate was evaporated to dryness. The resulting mixture was stirred with hexanes for 2 h. The white solid was filtered, followed by 3×20 mL hexanes wash and was dried in vacuo. White solid (7.90 g, 65% yield) was obtained. $^1$H NMR (in DMSO-$d_6$) indicated that it had two isomers (one major and one minor) in this solvent: δ6.73-7.13 (m, Ar—H, 3H); 2.98 (minor) and 2.71 (major) [m, $(CH_3)_2CH$—, total 2H], 2.11 (minor) and 1.67 (major) [s, N=C—$CH_3$, total 3H]; 1.05 (pseudo td, $(CH_3)_2CH$—, $^3J_{doublet}$=6.4 Hz). The structure of A below is a formal structure and may not completely represent the actual structure.

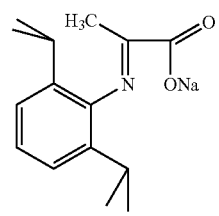

A

EXAMPLE 2

Synthesis of 1

In a drybox, A (0.500 g) was mixed with 0.251 g of nickel allyl chloride dimer in 30 mL THF. The color of the solution turned from deep red to yellow brown in a minute. The mixture was stirred for 14 h. THF was evaporated. The yellow solid was extracted with 30 mL toluene. The mixture was filtered through Celite®, followed by 3×5 mL toluene wash. The solution was concentrated to ca. 5 mL and was added to 50 mL of pentane. The solid product was filtered, washed with 3×10 mL pentane and dried in vacuo. Yellow solid was obtained (0.424 g, 66% yield). $^1$H NMR (in $CD_2Cl_2$): δ7.16-7.27 (m, Ar—H, 3H); 5.68 (hept, central allyl-H, 1H); 3.35 [m, overlapped syn-allyl-H (d, 1H) and $(CH_3)_2CH$—, (m, 1H), total 2H]; 2.92 (m, $(CH_3)_2CH-$, 1H); 2.35 (d, $^3J=13.2$ Hz, anti-terminal-allyl-H, 1H); 2.01 (d, $^3J=6.0$ Hz, syn-terminal-allyl-H, 1H); 1.91 (s, N=C—$CH_3$, total 3H]; 1.87 (d, $^3J=13.2$ Hz, anti-terminal-allyl-H, 1H); 1.33 (d, $^3J=6.4$ Hz, $(CH_3)_2CH-$, 3H); 1.27 (d, $^3J=6.5$ Hz, $(CH_3)_2CH-$, 3H); 1.19 (d, $^3J=6.4$ Hz, $(CH_3)_2CH-$, 3H); 1.09 (d, $^3J=6.5$ Hz, $(CH_3)_2CH-$, 3H). A single crystal of 1 was grown by slow evaporation of its methylene chloride/heptane solution. X-ray crystal structure of 1 was consistent with the proposed structure. The bond distance of the carbon-oxygen bond (the oxygen atom connected with Ni, $C_1$-$O_1$) was 1.277 (4) Å, indicating that it is a single bond. The bond distance of the carbonyl carbon-oxygen bond ($C_1$-$O_2$) was 1.229 (4) Å, indicating it was a double bond.

EXAMPLE 3

Synthesis of 2

In a drybox, A (1.500 g) was mixed with 0.753 g of nickel allyl chloride dimer in 50 mL THF. The mixture was stirred at RT for 5 h. THF was evaporated. The residue was extracted with 70 mL toluene. The mixture was filtered through Celite®, followed by 3×10 mL toluene wash. To this solution under stirring was added 2.9082 g $B(C_6F_5)_3$. The solution was allowed to stir for 2 h. The cloudy solution was filtered through Celite®, followed by 3×10 mL toluene wash. The filtrate was concentrated to dryness. The residue was dissolved in ca. 20 mL methylene chloride, followed by addition of ca. 150 mL pentane. The orange solid was filtered, washed with 3×10 mL pentane and dried in vacuo. Orange solid was obtained (1.450 g, 30% yield). $^1H$ NMR (in $CD_2Cl_2$): δ7.22-7.35 (m, Ar—H, 3H); 5.72 (hept, central allyl-H, 1H); 3.42 (d, syn-terminal-allyl-H, J=8.5 Hz, 1H); 3.22, 2.81 (m, $(CH_3)_2CH-$, 1H each]; 2.44 (d, $^3J=17.2$ Hz, anti-terminal-allyl-H, 1H); 2.35 (d, $^3J=8.2$ Hz, syn-terminal-allyl-H, 1H); 2.09 (s, N=C—$CH_3$, 3H]; 2.05 (d, $^3J=16.8$ Hz, anti-terminal-allyl-H, 1H); 1.36 (d, $^3J=8.4$ Hz, $(CH_3)_2CH-$, 3H); 1.30 (d, $^3J=8.4$ Hz, $(CH_3)_2CH-$, 3H); 1.25 (d, $^3J=8.4$ Hz, $(CH_3)_2CH-$, 3H); 1.15 (d, $^3J=8.5$ Hz, $(CH_3)_2CH-$, 3H). $^{19}F$ NMR in $CD_2Cl_2$: δ−135.74 (d, J=21.6 Hz, o-F, 2F); −160.60 (t, p-F, 1F); −166.40 (t, m-F, 2F). An orange-red single crystal of complex 2 was grown by slow evaporation of a methylene chloride/heptane solution. X-ray crystal structure was consistent with the proposed Zwitterion complex. The bond distance of the carbon-oxygen bond (the oxygen atom connected with Ni, $C_1$-$O_1$) was 1.241 (3) Å, indicating that it had become a double bond. The bond distance of the carbon-oxygen bond (the oxygen atom connected with boron $C_1$-$O_2$) was 1.278 (3) Å, indicating it had become a single bond. Anal. Calcd for $C_{36}H_{25}BF_{15}NNiO_2$: C, 50.39; H 2.94; N 1.63. Found: C, 50.08; H, 2.86; N, 1.60.

EXAMPLE 4

Synthesis of 3

In a drybox, to a $TiCl_4$ THF solution (0.3522 g in 20 mL THF) was added 0.5000 g A in portions at RT. The resulting mixture was allowed to stir overnight. The mixture was then filtered through Celite®, followed by 2×5 mL THF wash. The filtrate was evaporated to dryness. The resulting solid was dried in vacuo. Black crystalline solid (0.9026 g) was obtained.

EXAMPLE 5

Synthesis of 4

In a drybox, to a $TiCl_4$ THF solution (0.1761 g in 20 mL THF) was added 0.5000 g A in portions at RT. The resulting mixture was allowed to stir overnight. The mixture was then filtered through Celite®, followed by 2×5 mL THF wash. The filtrate was evaporated to dryness. The resulting solid was dried in vacuo. Dark green solid (0.6441 g, 92%) was obtained. $^1H$ NMR in THF-$d_8$: δ7.03-7.17 (m, Ar—H, 6H); 2.66 (hept, $(CH_3)_2CH-$, 4H), 1.90 (s, N=C—$CH_3$, 6H]; 1.13 (d, $^3J=7.0$ Hz, $(CH_3)_2CH-$, 12H); 1.11 (d, $^3J=6.8$ Hz, $(CH_3)_2CH-$, 12H).

EXAMPLE 6

Synthesis of 5

In a drybox, to a $ZrCl_4$ THF solution (0.4326 g in 20 mL THF) was added 0.5000 g A in portions at RT. The resulting mixture was allowed to stir overnight. The mixture was then filtered through Celite®, followed by 2×5 mL THF wash. The filtrate was evaporated to dryness. The resulting solid was dried in vacuo. Tan solid (0.9319 g) was obtained.

EXAMPLE 7

Synthesis of 6

In a drybox, to a $ZrCl_4$ THF solution (0.2163 g in 20 mL THF) was added 0.5000 g A in portions at RT. The resulting mixture was allowed to stir overnight. The mixture was then filtered through Celite®, followed by 2×5 mL THF wash. The filtrate was evaporated to dryness. The resulting solid was dried in vacuo. Pale yellow solid (0.6136 g) was obtained.

EXAMPLES 8-19

Ethylene Polymerization Using 1 and 2

In a drybox, a glass insert was loaded with the isolated Ni compounds. Solvent and optionally comonomers were added to the glass insert. A Lewis acid cocatalyst [typically $BPh_3$ or $B(C_6F_5)_3$] was often added to the solution. The insert was then capped and sealed. Outside of the drybox, the tube was placed under ethylene and was shaken mechanically at desired temperature listed in Table 1 for about 18 h. The resulted reaction mixture was blended with methanol, filtered, repeatedly washed with methanol and dried in vacuo.

Ethylene Polymerization by 3-6, in the Presence of PMAO

In a drybox, a glass insert was loaded with 0.02 mmol of the isolated Zr or Ti compound and 9 mL of 1,2,4-trichlorobenzene. It was then cooled to −30° C. PMAO [1 mL, 12.9 wt % (in Al) toluene solution] was added to the frozen solution. It was put in the −30° C. freezer. The insert was then capped and sealed. Outside of the drybox, the cold tube was placed under ethylene and was shaken mechanically at desired temperature listed in Table 1, condition IV, for about 18 h. Methanol (about 15 mL) and 2 mL conc. hydrochloric acid was added to the mixture. The polymer was isolated, washed with methanol several times and dried in vacuo.

Detailed conditions for the various polymerizations are given in Table 2.

TABLE 2

Polymerization Conditions

| Condition | |
|---|---|
| I | 0.02 mmol catalyst, 10 mL TCB, RT, 18 h, 6.9 MPa ethylene |
| II | 0.02 mmol catalyst, 6 mL TCB, 4 mL HA, 100° C., 18 h, 6.9 MPa ethylene, 40 eq $B(C_6F_5)_3$ |
| III | 0.02 mmol catalyst, 6 mL TCB, 4 mL HA, EGPEA or E-10-U, 120° C., 18 h, 6.9 MPa ethylene, 40 eq $B(C_6F_5)_3$ |
| IV | 0.02 mmol catalyst, 9 mL TCB, 1 mL PMAO-IP [12.9 wt % (in Al) in toluene], RT, 18 h, 6.9 MPa ethylene |

Polymer Characterization

The results of the ethylene polymerization and copolymerization catalyzed by 1-6 under different reaction conditions (See Table 2) are reported in Tables 3-6. The polymers were characterized by NMR, GPC and DSC analysis. A description of the methods used to analyze the amount and type of branching in polyethylene is given in previously incorporated U.S. Pat. No. 5,880,241. GPC's were run in trichlorobenzene at 135° C. and calibrated against polyethylene using universal calibration based on polystyrene narrow fraction standards. DSC was recorded between −100° C. to 150° C. at a rate of 10° C./minute. Data reported here are all based on second heat. Melting points were taken as the peak of the melting endotherm. $^1$H NMR of the polymer samples was run in tetrachloroethane-$d_2$ at 120° C. using a 500 MHz Bruker spectrometer.

TABLE 3

Ethylene Polymerization Under Condition I

| Example | Catalyst | Cocatalyst/ amt. | Yield (g) | #Me/ 1000CH$_2$ | m.p., (° C.) [ΔH$_f$] | Mw/PDI | TON |
|---|---|---|---|---|---|---|---|
| 8 | 1 | $B(C_6F_5)_3$/10 eq | 7.700 | 40 | 127 [106] | 248,950/2.2 second modal MP = 2,826 | 13,724 |
| 9 | 1 | $BPh_3$/10 eq | 0.570 | 10 | 129 [165] | 225,378/2.8 | 1,016 |
| 10 | 1 | none | 0 | / | / | / | / |
| 11 | 2 | none | 3.000 | 8 | 130 [156] | 232,371/4.0* | 5,347 |

*It has a small tail at MP = 674

TABLE 4

Ethylene/HA Copolymerization Under Condition II

| Example | Catalyst | Yield (g) | #Me/ 1000CH$_2$ | Mole % Comonomer | m.p., (° C.) [ΔH$_f$] | Mw/PDI | TON E/HA |
|---|---|---|---|---|---|---|---|
| 12 | 2 | 2.067* | 24 | 3.9 | 106 [120] | 7,664/2.3 | 3,009/121 |

*In addition to 2.067 g copolymer, HA homopolymer (0.567 g) was also produced.

TABLE 5

Ethylene Copolymerization under Condition III

| Ex. | Catalyst | Comonomer (Mole %) | Yield (g) | #Me/ 1000CH$_2$ | m.p. (° C.) (ΔH$_f$) | Mw/PDI | TON E/Comonomer |
|---|---|---|---|---|---|---|---|
| 13 | 2 | HA (4.4) | 2.543* | 29 | 97 [86.3] | 6,688/2.7 | 3,587/170 |
| 14 | 2 | EGPEA (2.0) | 3.182** | 22 | 100 [88.8] | 9,821/3.3 | 4,989/100 |
| 15 | 2 | E-10-U (2.3) | 18.252 | 24 | 93 [109] 115 | 17,455/6.2 | 27,689/640 |

*Contained 2.543 g copolymer and 0.772 g homopolymer of HA
**Contained 3.182 g copolymer and 1.963 g homopolymer of EGPEA

TABLE 6

Ethylene Polymerization under Condition IV

| Example | Catalyst | Yield (g) | m.p., (° C.) [$\Delta H_f$] | TON |
|---|---|---|---|---|
| 16 | 3 | 12.060 | 134 [132] | 21,496 |
| 17 | 4 | 11.607 | 134 [143] | 20,688 |
| 18 | 5 | 7.850 | 131 [133] | 13,992 |
| 19 | 6 | 7.317 | 132 [144] | 13,042 |

EXAMPLES 20-27

A 600 mL Parr® reactor was cleaned, heated up under vacuum, and then allowed to cool down under nitrogen. In a drybox, 8.1 mg (0.0094 mmole) of 2 and optionally Lewis acid were dissolved in 90 mL toluene and 60 mL E-10-U in a 300 mL RB flask. The flask was sealed using a rubber septum. Outside the drybox, an oil bath was prepared (see Table 7 for temperature). The RB flask was removed from the drybox. The solution was transferred via cannula into the autoclave under positive nitrogen pressure. The autoclave was sealed and pressurized to 690 kPa nitrogen. Nitrogen was then vented. The pressuring/venting was repeated two more times. At about 35 kPa nitrogen, the autoclave was stirred at about 600 RPM. Ethylene pressure (~4.8 MPa) was applied. The autoclave was quickly placed in the preheated bath. The pressure of the autoclave was adjusted to about 5.9 MPa and the temperature of the bath was adjusted to make the reaction mixture's temperature stabilize around the temperature listed in Table 7. It was stirred at this temperature and pressure for a time period indicated in Table 7. The heating source was removed and ethylene was vented. The autoclave was back-filled with 0.7 MPa nitrogen and nitrogen was vented after brief stirring. This was repeated two more times. The room temperature mixture was poured into 500 mL methanol, filtered, and washed with methanol. The resulting polymer was blended with methanol, filtered, and washed with methanol. The blending/washing procedure was repeated two more times. The white polymer was dried in vacuo overnight. Results are given in Table 7.

EXAMPLE 28

EHA Copolymerization Using a 600 cc Parr® Reactor

A 600 mL Parr® reactor was cleaned, heated up under vacuum, and then allowed to cool down under nitrogen. In a drybox, 16.1 mg of 2, 3.072 g (6 mmole, 320 eq to Ni catalyst) tris(pentafluorophenyl)boron, and 1.029 g (1.5 mmole, 80 eq to Ni catalyst) lithium tetrakis(pentafluorophenyl)borate were dissolved in 120 mL 1,2,4-trichlorobenzene and 30 mL (HA) in a 300 mL RB flask. It was sealed using a rubber septum. Outside the drybox, a 100° C. oil bath was prepared. The RB flask was removed from the drybox. The solution was transferred via cannula into the autoclave under positive nitrogen pressure. The autoclave was sealed and pressurized to 690 kPa nitrogen. Nitrogen was then vented. The pressuring/venting was repeated two more times. At about 35 kPa nitrogen, the autoclave was stirred at about 600 RPM. Ethylene pressure (~4.1 MPa) was applied. The autoclave was quickly placed in the preheated 100° C. bath. The pressure of the autoclave was adjusted to about 6.3 MPa and the temperature of the bath was adjusted to make the reaction temperature about 80° C. It was stirred at this temperature and pressure for 6 h. The heating source was removed and ethylene was vented. The autoclave was back-filled with 690 kPa nitrogen and nitrogen was vented after brief stirring. This was repeated two more times. The room temperature mixture was poured into 500 mL methanol, filtered, and washed with methanol. The resulting polymer was blended with methanol, filtered, and washed with methanol. It was dried in vacuo overnight. White polymer solid (5.321 g) was obtained. GPC (135° C., TCB): Mw=14,006; Mn=6,294; PDI=2.2. The polymer has a melting point of 113° C. (126.2 J/g) based on DSC. $^{13}$CNMR: 1.1 mole % HA incorporation. Total Me: 17.0 (9.1 Me; 1.7 Et; 1.5 Pr; 0.3 Bu; 4.9 Bu$^+$; 2.8 Am$^+$ and 0.6 Hex$^+$).

TABLE 7

Ethylene/E-10-U Copolymerizations

| Ex. | Temp. (° C.) | Time (hr) | Equiv. Lewis Acid | Yield (g) | E-10-U (Mole %) | #Me/1000CH$_2$ | m.p. (° C.) ($\Delta H_f$) | Mw/PDI |
|---|---|---|---|---|---|---|---|---|
| 20 | 80 | 2 | none | 12.08 | 1.4 | 13 | 114 (142.1) | 27,643/3.2 |
| 21 | 80 | 2 | 80 BPh$_3$ | 19.18 | 1.2 | 13 | 115 (145.8) | 29,669/2.7 |
| 22 | 80 | 4 | 80 BPh$_3$ | 36.63 | 1.4 | 13 | 113 (139.2) | 28,028/2.7 |
| 23 | 70 | 6 | 80 BPh$_3$ | 41.71 | 0.8 | 9 | 119 (149.3) | 37,279/2.4 |
| 24 | 60 | 6 | 80 BPh$_3$ | 27.17 | 0.7 | 8 | 120 (142.9) | 49,158/2.3 |
| 25 | 80 | 2 | 10 BPh$_3$ | 16.83 | 1.1 | 11 | 114.8 (153.8) | 27,497/3.3 |
| 26 | 80 | 2 | 10 B(C$_6$F$_5$)$_3$ | 36.81 | 1.0 | 14 | 115 (142.6) | 27,255/3.4 |
| 27 | 80 | 2 | 80 B(C$_6$F$_5$)$_3$ | 42.40 | 1.1 | 13 | 115 (144.2) | 26,940/2.8 |

EXAMPLES 29-33

TABLE 8

Ethylene/Polar Monomer Copolymerization Using 0.02 mmole 2, with or without B(C₆F₅)₃, with a Total Volume of 10 mL of TCB and Polar Monomer, under 80° C. at 3.4 MPa of Ethylene

| Ex | Catalyst | B(C₆F₅)₃ | Polar Monomer | Polar Monomer Volume (mL) | Yield (g) |
|---|---|---|---|---|---|
| 29 | 2 | 40 eq | 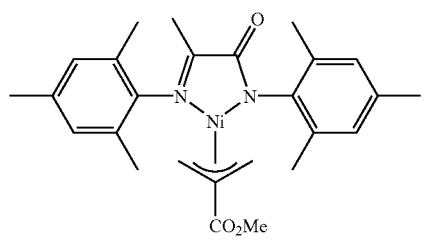 | 2 | 3.361 |
| 30 | 2 | 0 eq | 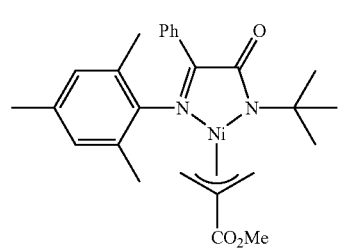 | 3 | 3.566 |
| 31 | 2 | 40 eq | $CH_2=CH(CH_2)_2C(O)CH_3$ | 3 | 0.116 |
| 32 | 2 | 40 eq | 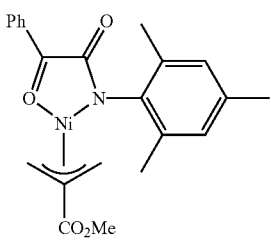 | 3 | 0.338 |
| 33 | 2 | 40 eq | $CH_2=CH(CH_2)_7C(CH_2O)_3CCH_3$ | 3 | 11.202 |

EXAMPLE 34

An ethylene/CO copolymerization using 0.02 mmole 2, 40 eq B(C₆F₅)₃, 10 mL TCB, at 100° C. under 2.8 MPa E/CO (9:1 ratio) was carried out for 16 h. The polymer yield was 0.048 g.

EXAMPLES 35-40

General Details of Ligand and Catalyst Synthesis for Cmpds G-1 through G-4

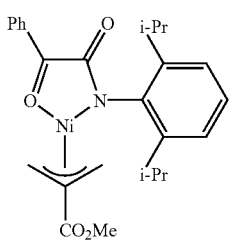

Nickel compounds G-1 and G-2 were synthesized according to eqs 1-4 and compounds G-3 and G-4 were synthesized according to eqs 1, 4 and 5.

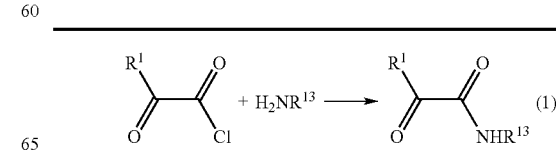

-continued

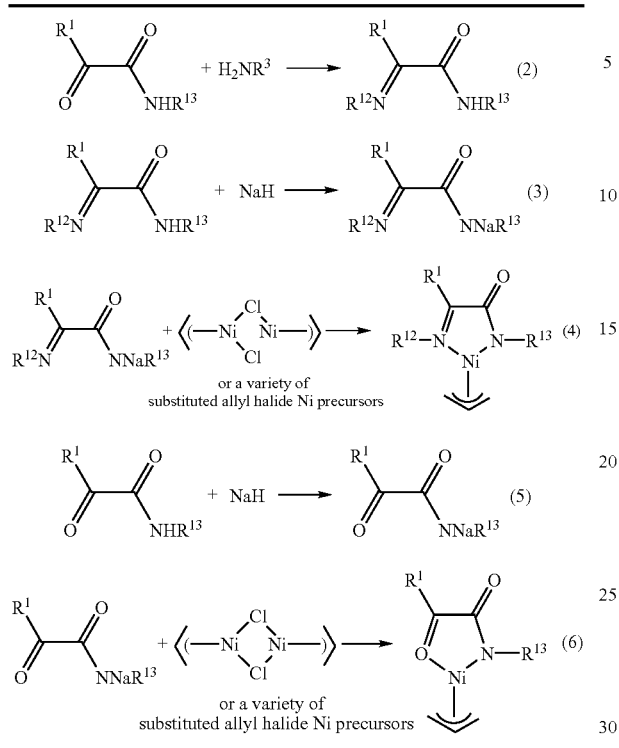

Precursors: Pyruvic acid chloride [Me—C(O)—C(O)—Cl] and phenylglyoxylic acid chloride [Ph—C(O)—C(O)—Cl], which were used for the ligand syntheses, were prepared by literature procedures: H. C. J. Ottenhedn, et al., *Synthesis*, 1975, 163-164. The acid chlorides were redistilled 3 times to achieve desirable purity.

Amido Compounds: The syntheses and characterization of amido derivatives of pyruvic acid chloride and phenylglyoxylic acid chloride are given in the examples below.

Imine Compounds: The keto-amido compounds were converted into imines according to standard literature methods: tom Dieck, H.; Svoboda, M.; Grieser, T. *Z. Naturforsch*, vol. 36b, p. 832 (1981). Typically, a small excess of aniline was added to the keto-amido compound in methanol together with a catalytic amount of formic acid. The reaction mixture was stirred for several days and the precipitate was collected on a frit, washed with methanol, and dried in vacuo to give the corresponding imino-amido compound.

Sodium Amides: Deprotonations of the amido compounds were carried out in a nitrogen-filled drybox. In general, the amido compound (several grams) was placed in a round bottom flask and dissolved in ~40 mL of THF. Excess NaH was added and the reaction mixture was stirred for several days. The reaction mixture was filtered through a frit with Celite® and the solvent was removed in vacuo to yield the sodium salt of the ligand.

Nickel Complexes: The nickel complexes G-1 through G-4 were synthesized by stirring a THF solution of the sodium salt of the corresponding ligand (1 equiv) and the appropriately substituted [(allyl)Ni(halide)]$_2$ precursor (0.5 equiv) in a nitrogen-filled drybox overnight. The solution was then filtered through a frit with dry Celite® and the solvent was removed in vacuo. The product was redissolved in Et$_2$O or toluene and the resulting solution was filtered. The solvent was removed in vacuo. The product was washed with pentane and then dried in vacuo.

EXAMPLE 35

2,6-Di-iso-propylanilide of Pyruvic Acid

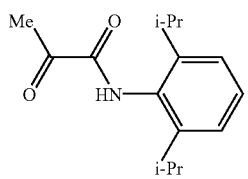

Pyruvic acid chloride (4.0 g, 0.038 mole) was dissolved in 200 mL of ethyl ether. A mixture of 7.3 g (0.041 mole) of 2,6-di-iso-propylaniline and 4.2 g (0.042 mole) of triethylamine in 100 mL of ethyl ether was then added dropwise to the solution of pyruvic acid chloride. The reaction mixture was stirred overnight and then the formed solids were removed by filtration. Removal of the solvent in vacuo yielded the product, which was further purified by recrystallization from pentane. The yield of the 2,6-di-iso-propylanilide of pyruvic acid was 2.9 g (31%) with m.p. 116.70° C. $^{13}$C NMR (CD$_2$Cl$_2$) δ160.61 (s, O═C—N), 198.09 (s, Me—C═O). GC/MS m/z 247; calcd: 247. Anal. Calcd. for C$_{15}$H$_{21}$NO$_2$: C, 72.77; H, 8.49; N, 5.66. Found: C, 72.54; H, 8.01; N, 5.97.

EXAMPLE 36

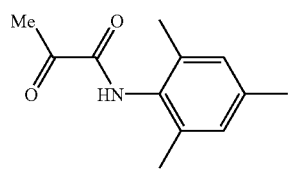

2,4,6-Trimethylanilide of Pyruvic Acid

Pyruvic acid chloride (4.0 g, 0.038 mole) was dissolved in 200 mL of ethyl ether. A mixture of 5.6 g (0.041 mole) of 2,4,6-trimethylaniline and 3.8 g (0.038 mole) of triethylamine in 100 mL of ethyl ether was added dropwise to the solution of pyruvic acid chloride. The reaction mixture was stirred overnight and then the formed solids were removed by filtration. Removal of the solvent in vacuo yielded the product, which was further purified by recrystallization from pentane. The yield of the 2,4,6-trimethylanilide of pyruvic acid was 3.9 g (51%) with m.p. 53.44° C. $^{13}$C NMR (CD$_2$Cl$_2$) δ159.28 (s, O═C—N), 198.07 (s, Me—C═O). GC/MS: m/z 205; calcd 205. Anal. Calcd. for C$_{12}$H$_{15}$NO$_2$: C, 70.16; H, 7.31; N, 6.86. Found: C, 71.03; H, 7.64; N, 7.04.

EXAMPLE 37

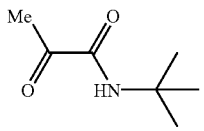

t-Butylamide of Pyruvic Acid

Pyruvic acid chloride (9.5 g, 0.089 mole) was dissolved in 200 mL of ethyl ether. A mixture of 7.18 g (0.098 mole) of tert-butylamine and 9.9 g (0.098 mole) of triethylamine in 100 mL of ethyl ether was added dropwise to the solution of pyruvic acid chloride. The reaction mixture was stirred overnight and then the formed solids were removed via filtration. Removal of the solvent in vacuo yielded the product, which was purified by distillation at 51° C./50 mm. The yield of the tert-butylamide of pyruvic acid was 3.7 g (29%). $^{13}$C NMR (CD$_2$Cl$_2$) $\delta$157.99 (s, O=C—N), 196.52 (s, Me—C=O). GC/MS: m/z 143; calcd 143. Anal. Calcd. for C$_7$H$_{13}$NO$_2$: C, 58.66; H, 9.08; N, 9.78. Found: C, 58.46; H, 9.15; N, 9.43.

EXAMPLE 38

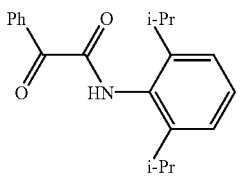

2,6-Di-i-propylanilide of Benzoylformic Acid

Benzoylformic chloride (5.0 g, 0.03 mole) was dissolved in 100 mL of ethyl ether. A mixture of 5.8 g (0.033 mole) of 2,6-di-i-propylaniline and 3.2 g (0.032 mole) of triethylamine in 100 mL of ethyl ether was added dropwise to the solution of benzoylformic acid chloride. The reaction mixture was stirred overnight and then the formed solids were removed by filtration. Removal of the solvent in vacuo yielded the product, which was further purified by recrystallization from pentane. The yield of the 2,6-di-i-propylanilide of benzoylformic acid was 5.4 g (59%) with m.p. 188.53° C. $^{13}$C NMR (CD$_2$Cl$_2$) $\delta$160.47 (s, O=C—N), 186.98 (s, Ph—C=O). GC/MS: m/z 309; calcd 309. Anal. Calcd. for C$_{20}$H$_{23}$NO$_2$: C, 77.57; H, 7.43; N, 4.52. Found: C, 77.35; H, 7.34; N, 4.53.

EXAMPLE 39

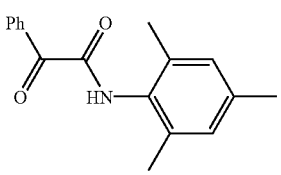

2,4,6-Trimethylanilide of Benzoylformic Acid

Benzoylformic chloride (5.2 g, 0.031 mole) was dissolved in 100 mL of ethyl ether. A mixture of 4.6 g (0.034 mole) of 2,4,6-trimethylaniline and 3.43 g (0.035 mole) of triethylamine in 100 mL of ethyl ether was added dropwise to the solution of benzoylformic acid chloride. The reaction mixture was stirred overnight and the formed solids were removed by filtration. Removal of the solvent in vacuo yielded the product, which was further purified by recrystallization from pentane. The yield of the 2,4,6-trimethylanilide of benzoylformic acid was 5.7 g (69%) with m.p. 208.48° C. $^{13}$C NMR (CD$_2$Cl$_2$) $\delta$161.33 (s, O=C—N), 188.94 (s, Ph—C=O). GC/MS: m/z 267; calcd 267. Anal. Calcd. for C$_{17}$H$_{17}$NO$_2$: C, 76.31; H, 6.36; N, 5.24. Found: C, 76.05; H, 6.13; N, 5.17.

EXAMPLE 40

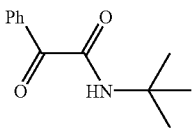

t-Butylamide of Benzoylformic Acid

Benzoylformic chloride (5.05 g, 0.0299 mole) was dissolved in 100 mL of ethyl ether. A mixture of 3.29 g (0.045 mole) of tert-butylamine and 3.33 g (0.033 mole) of triethylamine in 100 mL of ethyl ether was added dropwise to the solution of benzoylformic acid chloride. The reaction mixture was stirred overnight and the formed solids were then removed by filtration. Removal of the solvent in vacuo yielded the product, which was then purified by recrystallization from pentane. The yield of the tert-butylamide of benzoylformic acid was 3.12 g (51%) with m.p. 78.96° C. $^{13}$C NMR (CD$_2$Cl$_2$) $\delta$160.37 (s, O=C—N), 187.69 (s, Ph—C=O). GC/MS: m/z 205, calcd 205. Anal. Calcd. for C$_{12}$H$_{15}$NO$_2$: C, 70.15; H, 7.31; N, 6.82. Found: C, 69.92; H, 7.08; N, 6.79. The structure of this compound was confirmed by a single-crystal X-ray diffraction study.

EXAMPLES 41-48

General Details of the Polymerizations with Ni Cmpds G-1 through G-4: The polymerizations were carried out according to General Polymerization Procedure A below. Varying amounts of acrylate homopolymer are present in some of the isolated polymers. In Table 9, the yield of the polymer is reported in grams and includes the yield of the dominant ethylene/acrylate copolymer as well as the yield of any acrylate homopolymer that was formed. Molecular weights were determined by GPC, unless indicated otherwise. Mole percent acrylate incorporation and total Me were determined by $^1$H NMR spectroscopy, unless indicated otherwise. Mole percent acrylate incorporation is typically predominantly IC, unless indicated otherwise. The LiBArF used had 2.5 equiv of Et$_2$O coordinated.

General Procedure A for Ethylene Polymerizations and Copolymerizations: In a nitrogen-filled drybox, a 40 mL glass insert was loaded with the nickel compound and, optionally, a Lewis acid (e.g., BPh$_3$ or B(C$_6$F$_5$)$_3$) and borate (e.g., NaBAF or LiBArF) and any other specified cocatalysts. Next, the solvent was added to the glass insert followed by the addition of any co-solvents and then comonomers. The insert was greased and capped. The glass insert was then loaded in a pressure tube inside the drybox. The pressure tube was then sealed, brought outside of the drybox, connected to the pressure reactor, placed under the desired ethylene pressure and shaken mechanically. After the stated reaction time, the ethylene pressure was released and the glass insert was removed from the pressure tube. The polymer was precipitated by the addition of MeOH (~20 mL). The polymer was then collected on a frit and rinsed with MeOH and, optionally, acetone. The polymer was transferred to a pre-weighed vial and dried under vacuum overnight. The polymer yield and characterization were then obtained.

General Information Regarding Molecular Weight Analysis: GPC molecular weights are reported versus polystyrene standards. Unless noted otherwise, GPC's were run with RI detection at a flow rate of 1 mL/min at 135° C. with a run time of 30 min. Two columns were used: AT-806MS and WA/P/N 34200. A Waters RI detector was used and the solvent was TCB with 5 grams of BHT per gallon. Dual UV/RI detection GPC was run in THF at rt using a Waters 2690 separation module with a Waters 2410 RI detector and a Waters 2487 dual absorbance detector. Two Shodex columns, KF-806M, were used along with one guard column, KF-G. In addition to GPC, molecular weight information was at times determined by $^1$H NMR spectroscopy (olefin end group analysis) and by melt index measurements (g/10 min at 190° C.).

EXAMPLE 49

Values of LAIC for a Variety of Catalysts

The following values of LAIC were obtained by constructing models of the complexes with Dreiding Models and measuring the respective angles and distances. The structures shown are to indicate the connectivity of the model, but the measurements were taken on eht actual models.

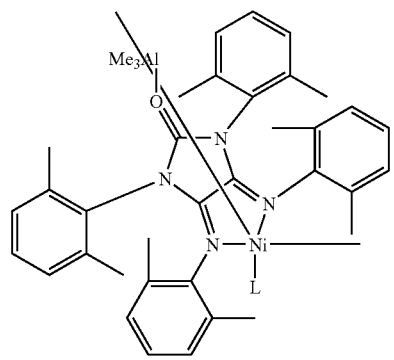

$\theta = 130°, \lambda = 7$ Å

TABLE 9

Ethylene Homopolymerizations and Ethylene/Acrylate Copolymerizations with Cmpds G-1 through G-4 (10 mL Total Volume of p-Xylene and Acrylate, 18 h)

| Ex. | Cmpd (mmol) | Acrylate mL | B(C$_6$F$_5$)$_3$ equiv (Borate equiv) | Press MPa | Temp °C. | Yield g | Acrylate Incorp. mol % | M.W. | Total Me |
|---|---|---|---|---|---|---|---|---|---|
| 41 | G-1 (0.005) | None | 40 (None) | 1.0 | 60 | 7.02 | — | $M_n(^1H) = 12,490$ | 32.4 |
| 42 | G-2 (0.005) | None | 40 (None) | 1.0 | 60 | 5.34 | — | $M_n(^1H) = 6,810$ | 34.0 |
| 43 | G-1 (0.002) | EGPEA 1 | 200 (NaBAF 100) | 6.9 | 120 | 0.668 | 3.42[a] 2.64 IC 0.78 EG | $M_p = 4,608$; $M_w = 5,421$; $M_n = 2,723$; PDI = 1.99 | 23.8 |
| 44 | G-2 (0.002) | EGPEA 1 | 200 (NaBAF 100) | 6.9 | 120 | 0.219 | 5.75[a] 3.73 IC 2.02 EG | $M_p = 4,789$; $M_w = 5,608$; $M_n = 2,872$; PDI = 1.95 | 26.4 |
| 45 | G-1 (0.02) | EGPEA 1 | 20 (NaBAF 10) | 6.9 | 120 | 1.66 | 2.4 | $M_p = 4,676$; $M_w = 5,912$; $M_n = 2,865$; PDI = 2.06 | 37.8 |
| 46 | G-2 (0.02) | EGPEA 1 | 20 (NaBAF 10) | 6.9 | 120 | 3.73 | 1.6 | $M_p = 4,517$; $M_w = 5,222$; $M_n = 1,985$; PDI = 2.63 | 44.9 |
| 47 | G-3 (0.005) | HA 1 | 80 (LiBArF 40) | 6.9 | 120 | 0.009 | 1.7 | $M_n(^1H) = 1,229$ | 75.3 |
| 48 | G-4 (0.005) | HA 1 | 80 (LiBArF 40) | 6.9 | 120 | 0.021 | 0.9[a] IC & EG | $M_n(^1H) = 5,034$ | 19.8 |

[a]The percent acrylate incorporation is an approximation due to the large amount of homopolymer present.

-continued

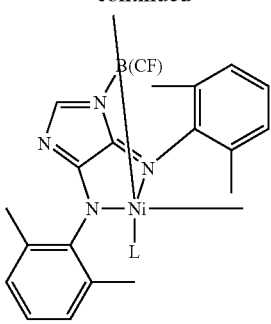

θ = 105°, λ = 5 Å

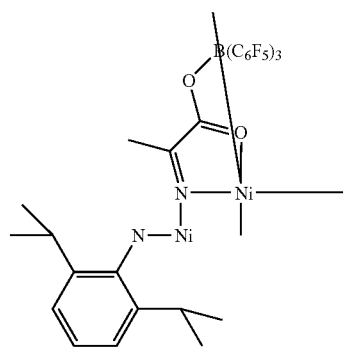

θ = 95°, λ = 4.5 Å

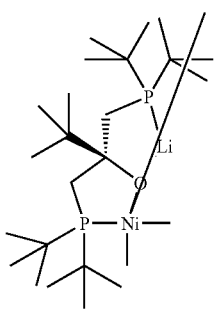

θ = 80°, λ = 3 Å

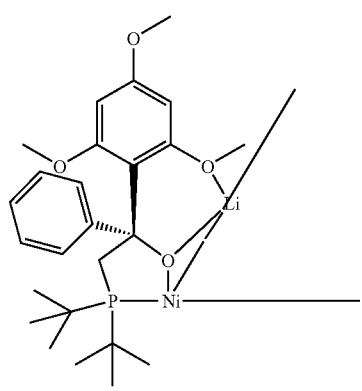

θ = 75°, λ = 3 Å

-continued

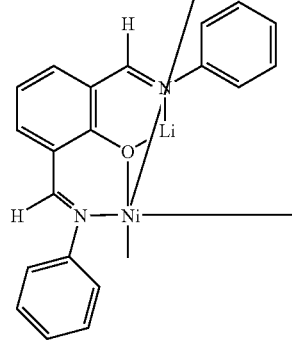

θ = 75°, λ = 3 Å

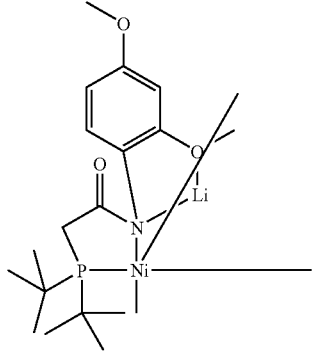

θ = 70°, λ = 3 Å

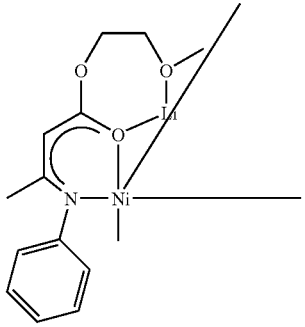

θ = 65°, λ = 3 Å

What is claimed is:

1. A process for the manufacture of a polar copolymer, wherein one or more hydrocarbon olefins, one or more polar olefins, and a polymerization catalyst system having a transition metal complex component containing a transition metal of groups 8-11 or a lanthanide metal, are contacted under polymerizing conditions to form said polar copolymer, wherein the transition metal complex component comprises a zwitterionic complex, which is an adduct of a neutral Lewis acid which is not covalently bound to a ligand of said transition metal complex component and a Lewis basic moiety of said ligand, wherein said ligand is a monoanionic bidentetate ligand and wherein said polar copolymer has an average degree of polymerization of 10 or more.

2. The process of claim 1, wherein said transition metal is Pd, Ni or Cu.

3. The process of claim 2, wherein said transition metal is Ni.

4. The process of claim 1, wherein a Lewis acid of said zwitterionic complex is a borane or an aluminane.

5. The process of claim 3, wherein a Lewis acid of said Zwitterionic complex is a borane or an aluminane.

6. The process of claim 4, wherein said Lewis acid is a tris(pentafluorophenyl)borane, triphenylborane, or a trihydrocarbylaluminum.

7. The process of claim 5, wherein said Lewis acid is a tris(pentafluorophenyl)borane, triphenylborane, or a trihydrocarbylaluminum.

8. The process of claim 1, wherein said hydrocarbon olefin is ethylene and said polar olefin is one or more of $H_2C\!\!=\!\!CHR^5CO_2R^6$, wherein $R^5$ is n-alkylene or a covalent bond, and $R^6$ is hydrocarbyl or substituted hydrocarbyl.

9. The process of claim 3, wherein said hydrocarbon olefin is ethylene and said polar olefin is one or more of $H_2C\!\!=\!\!CHR^5CO_2R^6$, wherein $R^5$ is n-alkylene or a covalent bond, and $R^6$ is hydrocarbyl or substituted hydrocarbyl.

10. The process of claim 3, wherein an ethylene pressure is about 700 kPa or more, and said process is run at about 50° C. to about 170° C.

11. The process of claim 8, wherein an ethylene pressure is about 700 kPa or more, and said process is run at about 50° C. to about 170° C.

* * * * *

UNITED STATES PATENT AND TRADEMARK OFFICE
CERTIFICATE OF CORRECTION

| | |
|---|---|
| PATENT NO. | : 7,683,147 B2 |
| APPLICATION NO. | : 10/272765 |
| DATED | : March 23, 2010 |
| INVENTOR(S) | : Lin Wang, Alex Sergey Ionkin and Lynda Kaye Johnson |

It is certified that error appears in the above-identified patent and that said Letters Patent is hereby corrected as shown below:

In Column 36, Claim 1, Line 60, please change "a Lewis basic moiety of said legend" to read -- a Lewis base which is part of said ligand --.

In Column 37, Claim 5, Line 2, please change "Zwitterionic" to read -- zwitterionic --.

Signed and Sealed this
Twenty-eighth Day of December, 2010

David J. Kappos
*Director of the United States Patent and Trademark Office*